US012636240B2

(12) United States Patent
Araki et al.

(10) Patent No.: US 12,636,240 B2
(45) Date of Patent: May 26, 2026

(54) ANTIPERSPIRANT COMPOSITION

(71) Applicant: Coty Inc., New York, NY (US)

(72) Inventors: Diego Takeshi Higa Araki, São Bernardo do Campo/ São Paulo (BR); Jose Elvecio Dos Santos Teixeira, Itapevi/ São Paulo (BR); Katia Nunes da Silva, Osasco— São Paulo (BR); Washington Romão Silva, Itapevi/ São Paulo (BR)

(73) Assignee: Coty Inc., New York, NY (US)

( * ) Notice: Subject to any disclaimer, the term of this patent is extended or adjusted under 35 U.S.C. 154(b) by 259 days.

(21) Appl. No.: 18/248,218

(22) PCT Filed: Oct. 5, 2021

(86) PCT No.: PCT/US2021/053643
§ 371 (c)(1),
(2) Date: Apr. 6, 2023

(87) PCT Pub. No.: WO2022/076469
PCT Pub. Date: Apr. 14, 2022

(65) Prior Publication Data
US 2023/0381076 A1 Nov. 30, 2023

Related U.S. Application Data

(60) Provisional application No. 63/089,603, filed on Oct. 9, 2020.

(51) Int. Cl.
| | |
|---|---|
| A61K 8/37 | (2006.01) |
| A61K 8/26 | (2006.01) |
| A61K 8/31 | (2006.01) |
| A61K 8/34 | (2006.01) |
| A61K 8/368 | (2006.01) |
| A61Q 15/00 | (2006.01) |

(52) U.S. Cl.
CPC .................. *A61K 8/37* (2013.01); *A61K 8/26* (2013.01); *A61K 8/31* (2013.01); *A61K 8/345* (2013.01); *A61K 8/368* (2013.01); *A61Q 15/00* (2013.01); *A61K 2800/34* (2013.01)

(58) Field of Classification Search
None
See application file for complete search history.

(56) References Cited

U.S. PATENT DOCUMENTS

| | | | |
|---|---|---|---|
| 2003/0113283 A1 | 6/2003 | Mattai et al. | |
| 2003/0161800 A1 | 8/2003 | Guenin et al. | |
| 2004/0126337 A1* | 7/2004 | Singleton | A61K 8/8152 424/59 |
| 2014/0199252 A1 | 7/2014 | Yarlagadda et al. | |

FOREIGN PATENT DOCUMENTS

| | | | | |
|---|---|---|---|---|
| CN | 103492029 | 1/2014 | | |
| CN | 108136027 | 6/2018 | | |
| CN | 110099663 | 8/2019 | | |
| CN | 116367811 | 6/2023 | | |
| EP | 2031235 A2 | 3/2009 | | |
| EP | 2949312 A1 | 12/2015 | | |
| FR | 2978034 A1* | 1/2013 | | A61K 8/062 |
| WO | WO-0174306 A2 | 10/2001 | | |
| WO | WO-0174325 A2 | 10/2001 | | |
| WO | WO-02087516 A3 | 3/2004 | | |
| WO | WO-2010068661 A1 | 6/2010 | | |
| WO | WO-2011146491 A2 | 11/2011 | | |
| WO | WO-2022076469 A1 | 4/2022 | | |
| WO | WO-2022076469 A8 | 4/2022 | | |

OTHER PUBLICATIONS

English translation for FR-2978034-A1 (Aubrun) (Year: 2013).*
"International Application Serial No. PCT/US2021/053643, International Search Report mailed Feb. 22, 2022", 4 pgs.
"International Application Serial No. PCT/US2021/053643, Written Opinion mailed Feb. 22, 2022", 5 pgs.
"Chinese Application Serial No. 202180068622.6, Decision of Rejection mailed Aug. 20, 2025", w/o English Translation, 6 pgs.
"Chinese Application Serial No. 202180068622.6, Office Action mailed Jun. 9, 2025", w/ English Translation, 14 pgs.
"Chinese Application Serial No. 202180068622.6, Response filed Aug. 5, 2025 to Office Action mailed Jun. 9, 2025", w/ English Claims, 21 pgs.
"International Application Serial No. PCT US2021 053643, International Preliminary Report on Patentability mailed Apr. 20, 2023", 7 pgs.
"Chinese Application Serial No. 202180068622.6, Office Action mailed Oct. 17, 2024", w Machine English Translation, 18 pgs.
"Chinese Application Serial No. 202180068622.6, Response filed Feb. 10, 2025 to Office Action mailed Oct. 17, 2024", w current English claims, 22 pgs.
"European Application Serial No. 21801344.9, Communication Pursuant to Article 94(3) EPC mailed Feb. 27, 2025", 3 pgs.

* cited by examiner

*Primary Examiner* — Sin J Lee
(74) *Attorney, Agent, or Firm* — Schwegman Lundberg & Woessner, P.A.

(57) ABSTRACT
Various aspects disclosed relate to an antiperspirant composition. The antiperspirant composition includes an isododecane component; an alkyl benzoate component; and a neopentyl glycol diheptanoate component.

18 Claims, 3 Drawing Sheets

ANTIPERSPIRANT COMPOSITION

CLAIM OF PRIORITY

This patent application is a U.S. National Stage Filing under 35 U.S.C. 371 from International Application No. PCT/US2021/053643, filed on Oct. 5, 2021, and published as WO 2022/076469 on Apr. 14, 2022, which application claims the benefit of priority to U.S. Application Ser. No. 63/089,603, filed Oct. 9, 2020, which is incorporated by reference herein in its entirety.

BACKGROUND

Consumers desire antiperspirant and deodorant compositions that provide a desired and long-lasting fragrance or scent each time the composition is applied or used. Particularly in the case of deodorants, consumers may also expect compositions that provide a scent that can mask or override other undesirable odors.

SUMMARY

Various aspects disclosed relate to an antiperspirant composition. The antiperspirant composition includes an isododecane component; an alkyl benzoate component; and a neopentyl glycol diheptanoate component.

Various further aspects disclosed relate to a method of making an antiperspirant composition. The antiperspirant composition includes an isododecane component; an alkyl benzoate component; and a neopentyl glycol diheptanoate component.

Various further aspects of the present disclosure relate to an assembly. The assembly includes spray container and an antiperspirant composition located in the spray container. The antiperspirant composition includes an isododecane component; an alkyl benzoate component; and a neopentyl glycol diheptanoate component.

BRIEF DESCRIPTION OF THE FIGURES

The drawings illustrate generally, by way of example, but not by way of limitation, various embodiments of the present invention.

DETAILED DESCRIPTION

Figures 1, 2:
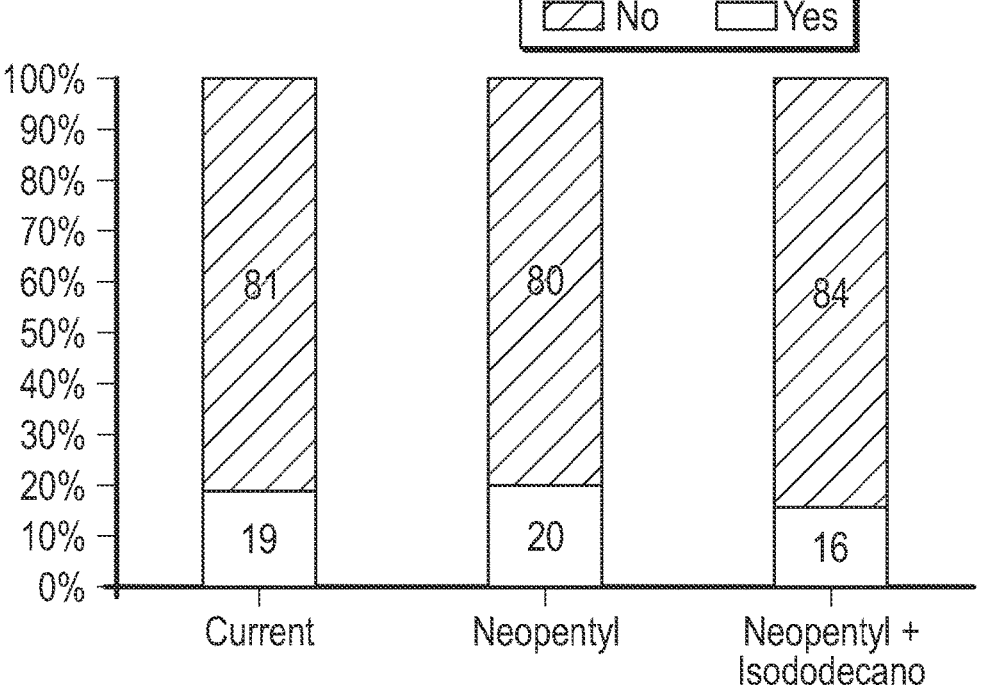
FIG. 1 is a graphical representation showing consumer perception of failure/interruption of spray discharge.
FIG. 2 is a graphical representation showing consumer perception of residue left on the actuator of a device including the disclosed compositions.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The polymers described herein can terminate in any suitable way. In some embodiments, the polymers can terminate with an end group that is independently chosen from a suitable polymerization initiator, —H, —OH, a substituted or unsubstituted $(C_1$-$C_{20})$hydrocarbyl (e.g., $(C_1$-$C_{10})$alkyl or $(C_6$-$C_{20})$aryl) interrupted with 0, 1, 2, or 3 groups independently selected from —O—, substituted or unsubstituted —NH—, and —S—, a poly(substituted or unsubstituted $(C_1$-$C_{20})$hydrocarbyloxy), and a poly(substituted or unsubstituted $(C_1$-$C_{20})$hydrocarbylamino).

It is found that consumers expect a high degree of performance of reducing perspiration when they use an antiperspirant composition. In addition to the high degree of performance, consumers desire long last action for reduction sweet According to various aspects of the present disclosure, an antiperspirant composition comprises an isododecane component, an alkyl benzoate component, and a neopentyl glycol diheptanoate component. Isododecane (an example of which is represented by CAS 31807-55-3) is generally understood to be a clear, colorless and odorless, volatile liquid, which makes it suitable for use in color cosmetics like mascara, eyeliner, lip products, antiperspirant or any product where improved wear properties and no residues are wanted. It does not leave an oily residue. Isododecane is a volatile, lipophilic component for deodorant sprays and hair care applications. It is a hydrocarbon ingredient used as a solvent. The alkyl benzoate component can be C12-15 alkyl benzoate (an example of which is represented by CAS 68411-27-8), which is generally understood to be a low-molecular weight ester of benzoic acid and C12-15 alcohols. C12-15 alkyl benzoate is a clear liquid that is practically odorless. In some examples, the alkyl benzoate component includes a C12 alkyl benzoate, a C13 alkyl benzoate, a C14 alkyl benzoate, a C15 alkyl benzoate, or a mixture thereof. Neopentyl glycol diheptanoate (an example of which is represented by CAS 68855-18-5) is generally understood to be a mixture of texture-enhancing ingredient neopentyl glycol and grape-derived fatty acid heptanoic acid.

Relative to the rest of the constituents of the antiperspirant composition the isododecane component can be in a range of from about 10 wt % to about 30 wt % of the antiperspirant composition about 15 wt % to about 20 wt %, less than, equal to, or greater than about 10 wt %, 11, 12, 13, 14, 15, 16, 17, 18, 19, 20, 21, 22, 23, 24, 25, 26, 27, 28, 29, or about 30 wt %. The alkyl benzoate component can be in a range of from about 15 wt % to about 30 wt % of the antiperspirant composition, about 20 wt % to about 25 wt %, less than, equal to, or greater than about 15 wt %, 16, 17, 18, 19, 20, 21, 22, 23, 24, 25, 26, 27, 28, 29, or about 30 wt %. The neopentyl glycol diheptanoate component can be in a range of from about 1 wt % to about 10 wt % of the antiperspirant composition, about 3 wt % to about 7 wt %, less than, equal to, or greater than about 3, 3.5, 4, 4.5, 5, 5.5, 6, 6.5, or about 7 wt %. The total concentration of the isododecane component, alkyl benzoate component, and neopentyl glycol diheptanoate component together can range from about 30 wt % to about 70 wt % of the antiperspirant composition, about 40 wt % to about 60 wt %, less than, equal to, or greater than about 30 wt %, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or about 70 wt %.

According to various aspects of the present disclosure, the antiperspirant composition is substantially free of cyclopentasiloxane. For example, the antiperspirant can include less than about 10 wt % cyclopentasiloxane, less than about 9 wt %, less than about 8 wt %, less than about 7 wt %, less than about 6 wt %, less than about 5 wt %, less than about 4 wt %, less than about 3 wt %, less than about 2 wt %, less than about 1 wt %, less than about 0.5 wt %, less than about 0.1 wt %, less than about 0.01 wt %, or less than about 0.001 wt %. in some aspects, the composition is completely free (e.g., includes 0 wt %) of cyclopentasiloxane. The disclosed isododecane component, alkyl benzoate component, and neopentyl glycol diheptanoate component, together, function to effectively replace cyclopentasiloxane in an antiperspirant while yielding an antiperspirant having similar, equal, or superior performance. Replacing cyclopentasiloxane can be desirable because, despite its performance in antiperspirant compositions, regulatory schemes seek to limit cyclopentasiloxane's use in cosmetic products. Therefore, it is important to find an effective substitute for cyclopentasiloxane. The inventors found that the combination of the isododecane component, alkyl benzoate component, and neopentyl glycol diheptanoate component, unexpectantly, provide an adequate replacement for cyclopentasiloxane. For example, an intensity or quantity at least one of spray discharge, amount of residue build-up in an underarm, amount of residue staining of clothing, perceived stickiness, antiperspirant protection, anti-odor protection, softness perception, or a combination thereof of the antiperspirant composition is substantially equal to that of the comparative antiperspirant composition including cyclopentasiloxane. Additionally, according to various aspects, substituting cyclopentasiloxane can help to increase the safety of the antiperspirant composition.

In comparing the disclosed antiperspirant compositions to those including cyclopentasiloxane, the combined amount of the isododecane component, alkyl benzoate component, and neopentyl glycol diheptanoate component is substantially equivalent to an amount of cyclopentasiloxane present in a comparative antiperspirant composition differing by including cyclopentasiloxane. Additionally, the combined amount of the isododecane component, alkyl benzoate component, and neopentyl glycol diheptanoate component is substantially equivalent to an amount of cyclopentasiloxane present in a comparative antiperspirant composition that differs only by including cyclopentasiloxane, with all other constituents being the same and in the same concentration.

The antiperspirant composition can take on many suitable forms. For example, according to various aspects, the antiperspirant composition is a stick antiperspirant, a body spray, a clear gel, or an aerosol antiperspirant. The antiperspirant composition can include a variety of additional components. For example, the antiperspirant composition can include a perfume. The perfume can be in a range of from about 0.001 wt % to about 5 wt % of the antiperspirant composition, about 0.01 wt % to about 0.05 wt %, less than, equal to, or greater than about 0.001 wt %, 0.005, 0.01, 0.05, 0.1, 0.5, 1, 1.5, 2, 2.5, 3, 3.5, 4, 4.5, or about 5 wt %. Perfumes or perfume raw materials can include compounds having a thiol moiety can include 5-methyl-5-sulfanyl-hexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanyl-prop-1-ene; methylsulfanyldisulfanylmethane; 1-methyldisulfanylpropane; ethane-1,2-dithiol; 1-(methyldisulfanyl)prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfa-nyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl)propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo

[3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; and 2-methyl-2-sulfanylpentan-1-ol. The compounds comprising sulfide moiety is selected from the group consisting of 1-butylsulfanylbutane; 2-methylsulfanylpyrazine; 2-methyl-3-methylsulfanylpyrazine; 2-(methylsulfanylmethyl)pyrazine; and mixtures thereof. Non-limiting examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; and 4-methyl-2-propan-2-yl-1,3-thiazole.

Non-limiting examples of further perfumes include compounds having an oxathiane moiety, which can include (2R,4S)-2-methyl-4-propyl-1,3-oxathiane, 2-methyl-4-propyl-1,3-oxathiane, and 2-pentyl-4-propyl-1,3-oxathiane Non-limiting examples of further perfumes include compounds containing oxygen, sulfur, and nitrogen include 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid.

More specific examples of the thiol moiety can include a-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; and 4-methoxy-2-methylbutane-2-thiol.

More specific examples of the sulfide moiety can include 1-butylsulfanylbutane; ethyl 3-methylsulfanylpropanoate; and 2-(methylsulfanylmethyl)furan.

More specific examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; and 1-(1,3-thiazol-2-yl)ethanone.

A more specific example of compounds having an oxathiane moiety can be (2R,4S)-2-methyl-4-propyl-1,3-oxathiane.

More specific examples of a compound comprising oxygen, sulfur, and nitrogen can include 2-(4-methyl-1,3-thiazol-5-yl)ethanol; 1-(1,3-thiazol-2-yl)ethanone; and 6-methyl-7-Oxa-1-thia-4-azaspiro[4.4]nonane.

In another example, the perfume raw materials can include sulfide moieties or thiazole moieties. The sulfide moieties can include 1-butylsulfanylbutane, 4,7,7-trimethyl-6-thiabicyclo[3.2.1]octane, and 2-methyl-3-methylsulfanylpyrazine. The thiazole moieties can include 1-(1,3-thiazol-2-yl)ethanone.

In another example, the perfume raw materials can be added to a base perfume in a group. Suitable groups can include group (a): 1-butylsulfanylbutane; (2R,4S)-2-methyl-4-propyl-1,3-oxathiane; and 4-methoxy-2-methylbutane-2-thiol; group (b): 2-(4-methyl-1,3-thiazol-5-yl)ethanol; 7-Oxa-1-thia-4-azaspiro[4.4]nonane; and 6-methyl-, 1-(1,3-thiazol-2-yl)ethanone; group (c): 2-(methylsulfanylmethyl)furan; ethyl 3-methylsulfanylpropanoate; and 1-butylsulfanylbutane; group (d): 5-methyl-5-sulfanylhexan-3-one; 5-methyl-2-(2-sulfanylpropan-2-yl)cyclohexan-1-one; and 2-(4-methyl-1-cyclohex-3-enyl)propane-2-thiol; group (e): 2-(2-methylpropyl)-1,3-thiazole; 2-(4-methyl-1,3-thiazol-5-yl)ethanol; and 4-methyl-2-propan-2-yl-1,3-thiazole; and group (f): (2R,4S)-2-methyl-4-propyl-1,3-oxathiane; 2-(4-methyl-1-cyclohex-3-enyl)propane-2-thiol; and (NE)-N-[(6E)-2,4,4,7-tetramethylnona-6,8-dien-3-ylidene]hydroxylamine.

Suitable perfume raw materials may be obtained from: Symrise GmbH, with offices located at Muhlenfeldstrasse 1, Holzminden, 37603, Germany; International Flavors & Fragrances Inc., a New York corporation having an address at 521 W 57th Street, New York, NY 10019; Givaudan Suisse SA a Swiss corporation having an address at 1214 Vernier, Switzerland; Firmenich Inc., with offices located at 250 Plainsboro Rd., Plainsboro Township, NJ 08536, United States; and Takasago International Corporation (USA), with offices located at 4 Volvo Drive, Rockleigh, NJ 07647, United States.

Antiperspirants compositions can also incorporate desirable scents through inclusion of perfumes and perfume raw materials in perfume delivery systems. Certain perfume delivery systems, methods of making certain perfume delivery systems, and the uses of such perfume delivery systems are disclosed in U.S. Pre-Grant Publication No. 2007/0275866 A1. The perfumes and perfume raw materials previously disclosed can be used in such perfume delivery systems. Such perfume delivery systems include: polymer-assisted delivery (PAD), molecule-assisted delivery (MAD), fiber-assisted deliver (FAD), amine-assisted delivery (AAD), cyclodextrin delivery system (CD), starch encapsulated accord (SEA), inorganic carrier delivery system (ZIC), and Pro-Perfume (PP). Examples of these perfume delivery systems are further described below.

In some aspects, the antiperspirant composition can include an odor entrapper. Where present, the odor entrapper is present in a range of from about 0.01 wt % to about 5 wt % of the antiperspirant composition, about 0.02 wt % to about 4 wt %, less than, equal to, or greater than about 0.01 wt %, 0.02, 0.05, 0.1, 0.5, 1, 1.5, 2, 2.5, 3, 3.5, 4, 4.5, or about 5 wt %.

Examples of suitable odor entrappers include S, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin includes six glucose units, the beta-cyclodextrin includes seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

In some aspects, the antiperspirant composition can further include a buffering agent. Where present, the buffering agent can be in a range of from about 0.001 wt % to about 0.75 wt % of the antiperspirant composition, about 0.01 wt % to about 0.5 wt %, less than, equal to, or greater than about 0.001 wt %, 0.005, 0.01, 0.05, 0.1, 0.5, or about 0.75 wt %.

A buffering agent can be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites. Suitable buffering agents include, for example, hydrochloric acid, sodium hydroxide, potassium hydroxide, and combinations thereof.

In some aspects of the present disclosure, the antiperspirant composition can include additional solubilizers. An additional solubilizer can be in a range of from about 0.01 wt % to about 5 wt % of the antiperspirant composition, about 0.01 wt % to about 3 wt %, less than, equal to, or greater than about 0.01 wt %, 0.05, 0.1, 0.5, 1, 1.5, 2, 2.5, 3, 3.5, 4, 4.5, or about 5 wt %.

Examples of suitable solubilizers include, for example, a surfactant, such as a no-foaming or low-foaming surfactant. Suitable surfactants are nonionic surfactants, cationic surfactants, amphoteric surfactants, zwitterionic surfactants, and mixtures thereof. Additionally, suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenate In some aspects of the present disclosure, the antiperspirant composition can include a preservative. Where present, the preservative can be a range of from about 0.0001 wt % to about 0.5 wt % of the antiperspirant composition, about 0.0003 wt % to about 0.1 wt %, less than, equal to, or greater than about 0.0001 wt %, 0.0003, 0.0005, 0.001, 0.005, 0.01, 0.05, 0.1, or about 0.5.

When included, the preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13@ from Induchem, Germall 115@ from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

In aspects where the antiperspirant composition is a spray or aerosol composition, the composition can include a carrier (such as an alcohol or water), a propellant, or both. The carrier can be present in range of from about 1 wt % to about 99.5 wt % of the composition, about 25 wt % to about 99.5 wt %, less than, equal to, or greater than about 1 wt %, 5, 10, 15, 20, 25, 30, 35, 40, 45, 50, 55, 60, 65, 70, 75, 80, 85, 90, 95, or 99.5 wt %.

The propellant can be present in a range of from about 15 wt % to about 85 wt % of the antiperspirant composition, about 20 wt % to about 40 wt %4, less than, equal to, or greater than about 15, 20, 25, 30, 35, 40, 45, 50, 55, 60, 65, 70, 75, 80, or about 85 wt %.

Examples of suitable propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane).

The antiperspirant composition can further include an antiperspirant active or deodorant active. The antiperspirant active can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, symdeo (2-Methyl 5-Cyclohexylpentanol) and mixtures thereof.

Aluminum salts include those that conform to the formula:

$$Al_2(OH)_aCl_b \cdot xH_2O,$$

a. wherein a is from about 2 to about 5;
b. the sum of a and b is about 6;
c. x is from about 1 to about 6; and
d. a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048, 229. Mixtures of aluminum salts are described in British Patent Specification 1,347,950. Zirconium salts for use in the anhydrous antiperspirant stick compositions include those which conform to the formula:

$$ZrO(OH)_{2-a}Cl_a \cdot xH_2O,$$

a. wherein a is from about 1.5 to about 1.87;
b. x is from about 1 to about 7; and
c. a and x may both have non-integer values.

These zirconium salts are described in Belgian Patent 825,146, Schmitz, issued Aug. 4, 1975. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948. Also suitable for use herein are enhanced efficacy aluminum-zirconium chlorohydrex-amino acid which typically has the empirical formula $Al_nZr(OH)_{[3n+4 \cdot m(n+1)]}(Cl)_{[m(n+1)]}-AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

According to some aspects of the present disclosure the antiperspirant composition can include an antiperspirant concentrate. In some aspects, alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

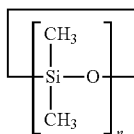

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide): MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

According to various embodiments of the present disclosure, the antiperspirant composition can further include a suspending agent. The suspending agent can be in a range of from about 0.1 wt % to about 5 wt % of the antiperspirant composition, about 0.1 wt % to about 2 wt %, less than, equal to, or greater than about 0.1 wt %, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5 wt %. where present, the suspending agent can include tearalkonium hectorite, which is designed to impart rheological control and suspension and is a suitable thickener for compositions of the present disclosure. It is a highly efficient rheological additive for intermediate to high polarity systems such as cyclomethicones, esters, triglycerides, vegetable oils, alcohols and ketones.

According to various embodiments of the present disclosure, the antiperspirant composition can further include an oil absorbent. The oil absorbent can be present in a range of from about 0.001 wt % to about 3 wt % of the antiperspirant composition, about 0.01 wt % to about 0.5 wt %, less than, equal to, or greater than about 0.001 wt %, 0.005, 0.0.01, 0.05, 0.1, 0.5, 1, 1.5, 2, 2.5, or about 3 wt %. Examples of suitable oil absorbents include aluminum starch octenylsuccinate (also known as modified corn starch), tapioca starch, silica, and polymethylsilsesquioxane Other components or constituents can be added to the antiperspirant composition that are not specifically articulated herein. Beyond the components described herein the balance of the antiperspirant composition can be accounted for by water. The water can be present in a range of from about 5 wt % to about 80 wt % of the antiperspirant composition, about 45 wt % to about 70 wt %, less than, equal to, or greater than about 5 wt %, 10, 15, 20, 25, 30, 35, 40, 45, 50, 55, 60, 65, 70, 75, or about 80 wt %.

The antiperspirant composition described herein can be formed by combining any of the constituents described herein with the isododecane component; alkyl benzoate component; and the neopentyl glycol diheptanoate component.

EXAMPLES

Various embodiments of the present disclosure can be better understood by reference to the following Examples which are offered by way of illustration. The present disclosure is not limited to the Examples given herein.

Spray Deodorant Compositions

TABLE 1

Composition 1 ("Neopentyl + Isododecane")

| INCI NAME | Wt % |
|---|---|
| Diisopropyl Adipate | 0.5-1 |
| BHT | 0.001-0.009 |
| C12-15 Alkyl Benzoate | 3-6 |
| Disteardimonium Hectorite | 0.30-0.60 |
| Propylene Carbonate | 0.05-0.20 |
| Neopentyl Glycol Diheptanoate | 0.50-0.90 |
| Aluminum Chlorohydrate | 3-8 |
| Methyldihydrojasmonate | 0.005-0.200 |
| Dipropylene Glycol | 0.001-0.009 |
| Ethylene Brassylate | 0.001-0.009 |
| Tetramethyl Acetyloctahydronaphthalenes | 0.0010-0.0050 |
| PEG-30 Dipolyhydroxystearate | 0.03-0.08 |
| Lauryl Glucoside | 0.03-0.08 |
| Glycerin | 0.050-0.090 |
| Isododecane | 1-3 |
| Propane/Butane/Isobutane | 70-90 |

TABLE 2

Composition 2 ("Neopentyl")

| INCI NAME | Wt % |
|---|---|
| Diisopropyl Adipate | 0.5-1 |
| BHT | 0.001-0.009 |
| C12-15 Alkyl Benzoate | 3-6 |
| Disteardimonium Hectorite | 0.30-0.60 |
| Propylene Carbonate | 0.05-0.20 |
| Neopentyl Glycol Diheptanoate | 0.50-0.90 |
| Aluminum Chlorohydrate | 3-8 |
| Methyldihydrojasmonate | 0.005-0.200 |
| Dipropylene Glycol | 0.001-0.009 |
| Ethylene Brassylate | 0.001-0.009 |
| Tetramethyl Acetyloctahydronaphthalenes | 0.0010-0.0050 |

TABLE 2-continued

| Composition 2 ("Neopentyl") | |
| --- | --- |
| INCI NAME | Wt % |
| PEG-30 Dipolyhydroxystearate | 0.03-0.08 |
| Lauryl Glucoside | 0.03-0.08 |
| Glycerin | 0.050-0.090 |
| Propane/Butane/Isobutane | 70-90 |

TABLE 3

| Comparative Composition 1 ("Current") | |
| --- | --- |
| INCI NAME | Wt % |
| Diisopropyl Adipate | 0.5-0.9 |
| BHT | 0.003-0.009 |
| Dimethicone | 0.5-0.9 |
| Cyclopentasiloxane | 5-8 |
| Disteardimonium Hectorite | 0.3-0.6 |
| Propylene Carbonate | 0.05-0.20 |
| 2-Methyl 5-Cyclohexylpentanol | 0.005-0.020 |
| Aluminum Chlorohydrate | 3-6 |
| Methyldibydrojasmonate | 0.005-0.02 |
| Dipropylene Glycol | 0.001-0.009 |
| Ethylene Brassylate | 0001-0.009 |
| Tetramethyl Acetyloctahydronaphthalenes | 0.0010-0.004 |
| Polyglyceryl-2 Dipolyhydroxystearate | 0.05-0.20 |
| Lauryl Glucoside | 0.05-0.3 |
| Glycerin | 0.05-0.20 |
| Aqua | 0.05-0.20 |
| Citric Acid | 0.0010-0.005 |
| Propane/Butane/Isobutane | 75-90 |

Consumer Feedback

To determine relative performance of Compositions 1 and 2, relative to Comparative Composition 1, a consumer panel was created to test all three compositions. The consumer panel included 96 men between the ages of 18-55. Each composition was tested at the panelist's respective homes continuously for one week. Various properties of the compositions were rated on a 7-point scale.

Taken as a whole, consumers indicated that the performance of compositions 1 and 2 were adequate, equal to, or better than the performance of comparative composition 1, which unlike compositions 1 and 2 included cyclopentasiloxane. Consumer panel results with average values listed are shown below.

The study was conducted as described below:

Definitions

CTI: Consumer Technical Institute
R&D: Research and Development
ICF: Informed Consent Form
QP&B: Questionnaire of Practices and Behaviors
HUT: Home Use Test Evaluation Steps During the HUT, the consumers use the product at home in accordance with normal conditions of use of the product. In the HUT sensory evaluation of aerosol deodorant antiperspirant (AP) spray each participant uses each sample for one week and the samples are exchanged at CTI.

Type of Test

Monadic and sequential evaluation, i.e., the sample is evaluated individually each week. The HUT sensory evaluation is performed with 100 participants aerosol deodorant AP Spray users.

Samples Preparation and Submission

The aerosol deodorant samples are prepared by R&D, and provided in the amount of 110 units.

At least 24 hours before the evaluation, the samples shall remain stored at the same room temperature of the test execution site.

The samples are coded with random numbers of three digits non-repeated, blindly submitted and balanced among participants, so that all samples appear the same number of times in a given position/week, but in random order for each participant.

Conducting the Study

The participant receives the sample that will be evaluated in the first week of use, together with the evaluation questionnaire.

The following guidelines are provided to the participants.

Number of the participant's visit to CTI, with a difference of 1 week between visits; and time he/she will stay at the CTI facilities (approximately 30 minutes per visit);

Instructions to use the product included on the label;

Use only the study's sample during the evaluation period;

Only the participant should use the sample, and it should not be shared with family, friends, co-workers and others;

Ask the participant to start the sample's evaluation on the day of each visit, but complete the evaluation questionnaire provided on the day of return or one day before the defined return date for the exchange of samples;

Inform volunteers that returning samples is mandatory. If no product remains, he/she must return the empty package to CTI.

CTI does not accept the return of samples/questionnaires/receipt of vouchers by third parties.

| ATTRIBUTES | | |
| --- | --- | --- |
| ATTRIBUTES | | SCALE |
| General Liking | Hedonic of | 1 = Disliked very much |
| Actuator button | seven points | 2 = Disliked |
| Spray discharge | | 3 = Disliked slightly |
| Spray coverage area | | 4 = Neither like nor dislike |
| Drying | | 5 = Liked slightly |
| Fragrance | | 6 = Liked |
| | | 7 = Liked very much |
| Spray discharge intensity | Seven points Just About | 1 = Much weaker than I like it 2 = Weaker than I like it |
| Quantity of product left on the spray discharge | Right (JAR) Scale | 3 = Slightly weaker than I like it 4 = Just as I like it 5 = Slightly stronger than I like it |
| Fragrance Intensity | | 6 = Stronger than I like it |
| Lasting Fragrance | | 7 = Much stronger than I like it |
| Residue buildup on the underarm | Intensity of seven points | 1 = None/extremely Low 2 = Very Low |
| Residue/stains of | | 3 = Low |

-continued

ATTRIBUTES

| ATTRIBUTES | | SCALE |
|---|---|---|
| clothing | | 4 = Medium/Average |
| Stickiness | | 5 = High |
| Anti-Perspirant | | 6 = Very High |
| Protection | | 7 = Extremely High |
| Anti-Odor Protection | | |
| Ease of use the | Intensity of | 1 = Very difficult |
| actuator button | seven points | 2 = Difficult |
| | | 3 = Slightly difficult |
| | | 4 = Neither easy/nor difficult |
| | | 5 = Slightly easy |
| | | 6 = Easy |
| | | 7 = Very easy |
| Faillure/Interruption | Binary Scale | 1 = Yes |
| of Spray discharge | | 2 = No |
| Residue remaining in | | |
| the actuator button | | |
| Discomfort | | |
| Product's approval | | |

Analysis of Results

The data of the studies was collected using the Fizz software and the results compared for each attribute and evaluated through statistical analysis using the Fizz Calculation and XLSTAT softwares:

| ATTRIBUTES | SOFTWARE | STATISTICAL ANALYSIS |
|---|---|---|
| General Liking Actuator button Ease of use the actuator button Spray discharge Spray coverage area Drying Fragrance Residue buildup in the underarm Residue/stains of clothing Stickiness Anti-perspirant protection Anti-odor protection | Fizz Calculation | For two sample tests: Student t test paired at the minimum significance level of 5% (95% confidence level); For tests with more than two samples: ANOVA (Tukey) test paired at the minimum significance level of 5% (95% confidence level); |
| Top Two Box of General Liking Spray discharge intensity Quantity of product left on the spray discharge Fragrance intensity Lasting fragrance Faillure/interruption of spray discharge Residue remaining in the actuator button Discomfort Product's approval | XLSTAT | For n samples: Parametric tests: comparison of proportions at the minimum significance level of 5% (95% confidence level); |

-continued

| ATTRIBUTES | SOFTWARE | STATISTICAL ANALYSIS |
|---|---|---|
| Preference | Fizz Calculation | For 2 samples: proportion tests (z test for 1 proportion) at a minimum significance level of 5% (95% confidence level); For n samples: Friedman's non-parametric ordering test, at the minimum significance level of 5% (95% confidence level); |

Results

TABLE 4

| | Current | Neopentyl | Neopentyl + Isododecane |
|---|---|---|---|
| GENERAL LIKING | 5.6 | 5.5 | 5.6 |
| ACTUATOR BUTTON | 6.1 | 6.0 | 5.9 |
| SPRAY DISCHARGE | 5.8 | 5.3 | 5.6 |
| SPRAY COVERAGE AREA | 5.8 ab | 5.7 b | 6.0 a |
| DRYING | 5.8 | 5.7 | 5.8 |
| FRAGRANCE/PERFUME | 5.6 | 5.3 | 5.6 |
| RESIDUE BUILDUP IN UNDERARM | 2.3 | 2.4 | 2.3 |
| RESIDUE/STAINING OF CLOTHING | 1.9 | 1.9 | 1.7 |
| STICKINESS | 2.1 | 2.2 | 2.2 |
| ANTIPERSPIRANT PROTECTION | 4.7 | 4.6 | 4.8 |
| ANTI-ODOR PROTECTION | 4.7 | 4.7 | 4.7 |

Tests showed that there was no significant difference between the samples concerning proportion of failure/interruption of spray discharge. This is shown graphically in FIG. 1

Tests showed that there was no significant difference between the samples concerning residue left on the actuator. This is shown graphically in FIG. 2

Figure 3:
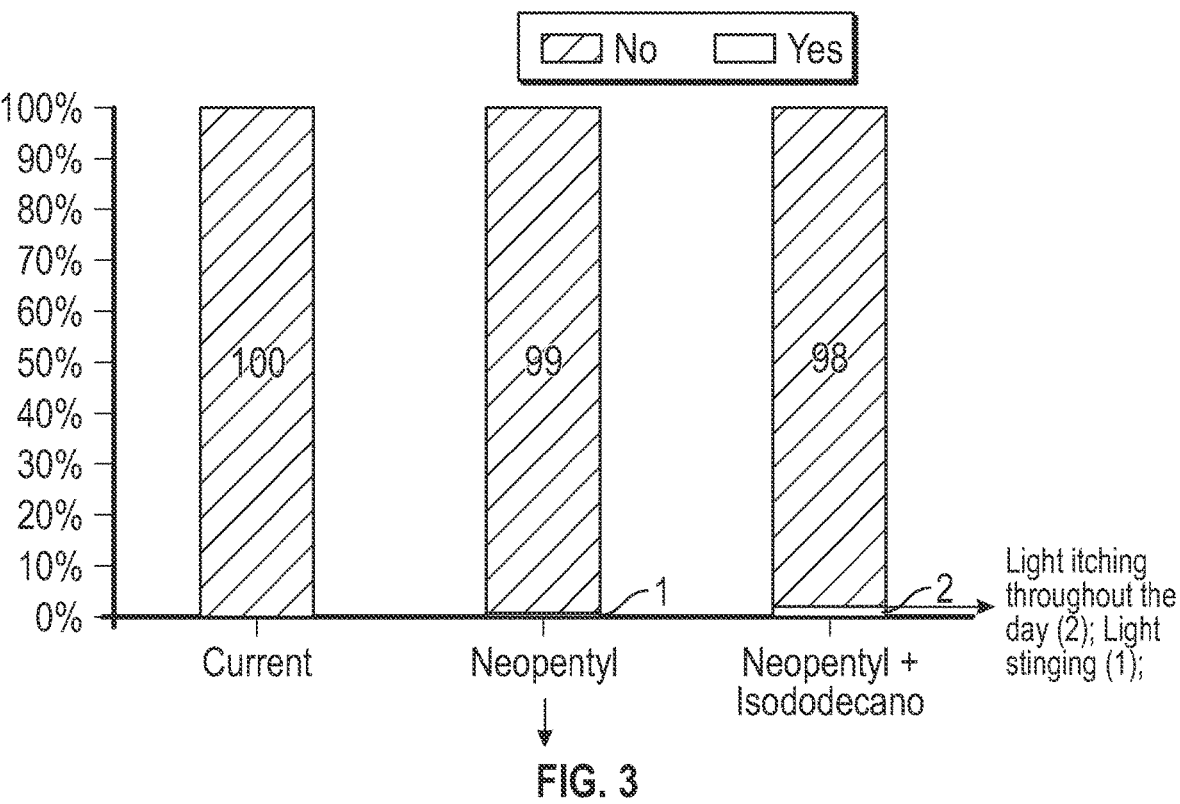
FIG. 3 is a graphical representation showing consumer perception between the samples concerning perception of discomfort sensation.

Tests showed that there was no significant difference between the samples concerning perception of Discomfort Sensation. This is shown graphically in FIG. 3.

Figure 4:
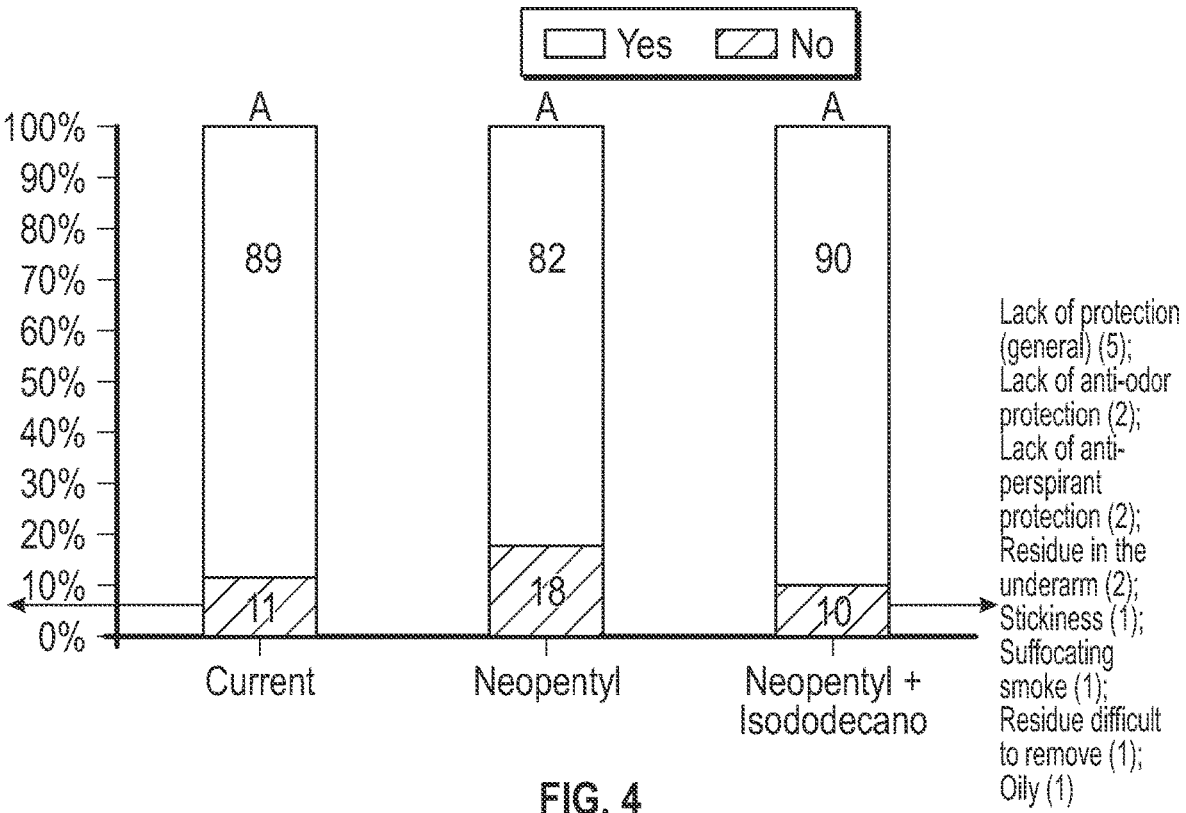
FIG. 4 is a graphical representation showing consumer perception between the samples concerning perception of a perceived difference regarding softness.

Tests showed that was no significant difference between the samples concerning product's approval as a deodorant antiperspirant. This is shown graphically in FIG. 4.

Figure 5:
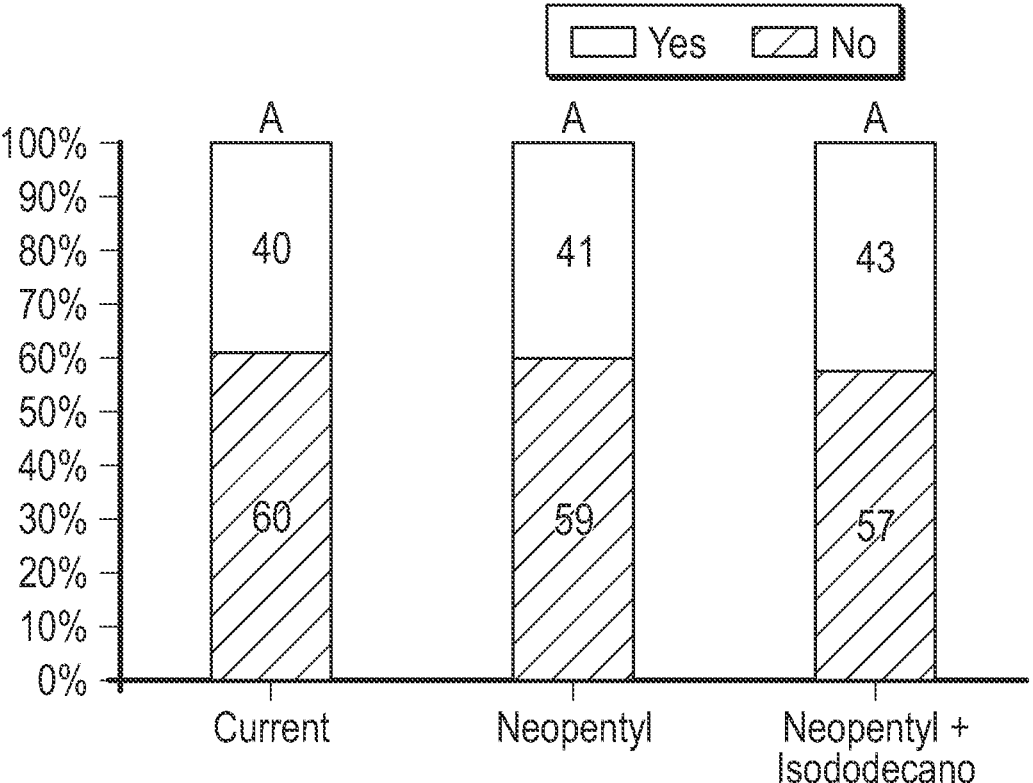
FIG. 5 is a graphical representation showing that there was no significant difference between the samples concerning the proportion of a perceived difference regarding softness.

Tests showed that there was no significant difference between the samples concerning the proportion of a perceived difference regarding softness. This is shown graphically in FIG. 5.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Exemplary Embodiments

The following exemplary embodiments are provided, the numbering of which is not to be construed as designating levels of importance.

Aspect 1 provides an antiperspirant composition comprising:
an isododecane component;
an alkyl benzoate component; and
a neopentyl glycol diheptanoate component.

Aspect 2 provides the antiperspirant composition of Aspect 1, wherein the alkyl benzoate component is a C12-15 alkyl benzoate.

Aspect 3 provides the antiperspirant composition of any one of Aspects 1 or 2, wherein the alkyl benzoate component comprises a C12 alkyl benzoate, a C13 alkyl benzoate, a C14 alkyl benzoate, a C15 alkyl benzoate, or a mixture thereof.

Aspect 4 provides the antiperspirant composition of any one of Aspects 1-3, wherein:
the isododecane component is in a range of from about 10 wt % to about 30 wt % of the antiperspirant composition;
the alkyl benzoate component is in a range of from about 15 wt % to about 30 wt % of the antiperspirant composition; and
the neopentyl glycol diheptanoate component is in a range of from about 1 wt % to about 10 wt % of the antiperspirant composition.

Aspect 5 provides the antiperspirant composition of any one of Aspects 1-4, wherein:
the isododecane component is in a range of from about 15 wt % to about 20 wt % of the antiperspirant composition;
the alkyl benzoate component is in a range of from about 20 wt % to about 25 wt % of the antiperspirant composition; and
the neopentyl glycol diheptanoate component is in a range of from about 3 wt % to about 7 wt % of the antiperspirant composition.

Aspect 6 provides the antiperspirant composition of any one of Aspects 1-5, wherein the isododecane component, alkyl benzoate component, and neopentyl glycol diheptanoate component together range from about 30 wt % to about 70 wt % of the antiperspirant composition.

Aspect 7 provides the antiperspirant composition of any one of Aspects 1-6, wherein the isododecane component, alkyl benzoate component, and neopentyl glycol diheptanoate component together range from about 40 wt % to about 60 wt % of the antiperspirant composition.

Aspect 8 provides the antiperspirant composition of any one of Aspects 1-7, wherein the antiperspirant composition is substantially free of cyclopentasiloxane.

Aspect 9 provides the antiperspirant composition of any one of Aspects 1-8, wherein the antiperspirant composition is free of cyclopentasiloxane.

Aspect 10 provides the antiperspirant composition of any one of Aspects 1-9, wherein the combined amount of the isododecane component, alkyl benzoate component, and neopentyl glycol diheptanoate component is substantially equivalent to an amount of cyclopentasiloxane present in a comparative antiperspirant composition differing by comprising cyclopentasiloxane.

Aspect 11 provides the antiperspirant composition of any one of Aspects 1-10, wherein the combined amount of the isododecane component, alkyl benzoate component, and neopentyl glycol diheptanoate component is substantially equivalent to an amount of cyclopentasiloxane present in a comparative antiperspirant composition differing only by comprising cyclopentasiloxane.

Aspect 12 provides the antiperspirant composition of any one of Aspects 1-11, wherein the antiperspirant composition is a stick antiperspirant, a body spray, a clear gel, or an aerosol antiperspirant.

Aspect 13 provides the antiperspirant composition of any one of Aspects 1-12, further comprising a perfume.

Aspect 14 provides the antiperspirant composition of Aspect 13, wherein the perfume is in a range of from about 0.001 wt % to about 0.1 wt % of the antiperspirant composition.

Aspect 15 provides the antiperspirant composition of any one of Aspects 13 or 14, wherein the perfume is in a range of from about 0.01 wt % to about 0.05 wt % of the antiperspirant composition.

Aspect 16 provides the antiperspirant composition of any one of Aspects 1-15, further comprising water.

Aspect 17 provides the antiperspirant composition of Aspect 16, wherein the water is present in a range of from about 5 wt % to about 80 wt % of the antiperspirant composition.

Aspect 18 provides the antiperspirant composition of any one of Aspects 16 or 17, wherein the water is present in a range of from about 45 wt % to about 70 wt % of the antiperspirant composition.

Aspect 19 provides the antiperspirant composition of any one of Aspects 1-18, further comprising a deodorant active.

Aspect 20 provides the antiperspirant composition of Aspect 19, wherein the deodorant active is present in a range of from about 0.001 wt % to about 20 wt % of the antiperspirant composition.

Aspect 21 provides the antiperspirant composition of any one of Aspects 19 or 20, wherein the deodorant active is present in a range of from about 1 wt % to about 5 wt % of the antiperspirant composition.

Aspect 22 provides the antiperspirant composition of any one of Aspects 1-21, further comprising an odor entrapper deodorant active.

Aspect 23 provides the antiperspirant composition of Aspect 22, wherein the odor entrapper is present in a range of from about 0.01 wt % to about 5 wt % of the antiperspirant composition.

Aspect 24 provides the antiperspirant composition of any one of Aspects 22 or 23, wherein the odor entrapper is present in a range of from about 0.02 wt % to about 4 wt % of the antiperspirant composition.

Aspect 25 provides the antiperspirant composition of any one of Aspects 1-24, further comprising a buffering agent.

Aspect 26 provides the antiperspirant composition of Aspect 25, wherein the buffering agent is present in a range of from about 0.001 wt % to about 0.75 wt % of the antiperspirant composition.

Aspect 27 provides the antiperspirant composition of any one of Aspects 25 or 26, wherein the buffering agent is present in a range of from about 0.01 wt % to about 0.5 wt % of the antiperspirant composition.

Aspect 28 provides the antiperspirant composition of any one of Aspects 1-27, further comprising a solubilizer.

Aspect 29 provides the antiperspirant composition of Aspect 28, wherein the solubilizer is present in a range of from about 0.01 wt % to about 5 wt % of the antiperspirant composition.

Aspect 30 provides the antiperspirant composition of any one of Aspects 28 or 29, wherein the solubilizer is present in a range of from about 0.01 wt % to about 3 wt % of the antiperspirant composition.

Aspect 31 provides the antiperspirant composition of any one of Aspects 1-30, further comprising a preservative.

Aspect 32 provides the antiperspirant composition of Aspect 31, wherein the preservative is present in a range of from about 0.0001 wt % to about 0.5 wt % of the antiperspirant composition.

Aspect 33 provides the antiperspirant composition of any one of Aspects 31 or 32, wherein the preservative is present in a range of from about 0.0003 wt % to about 0.1 wt % of the antiperspirant composition.

Aspect 34 provides the antiperspirant composition of any one of Aspects 1-33, further comprising a propellant.

Aspect 35 provides the antiperspirant composition of Aspect 34, wherein the propellant is present in a range of from about 15 wt % to about 85 wt % of the antiperspirant composition.

Aspect 36 provides the antiperspirant composition of any one of Aspects 34 or 35, wherein the propellant is present in a range of from about 20 wt % to about 40 wt % of the antiperspirant composition.

Aspect 37 provides the antiperspirant composition of any one of Aspects 1-36, further comprising a concentrate.

Aspect 38 provides the antiperspirant composition of Aspect 37, wherein the concentrate comprises an alcohol.

Aspect 39 provides the antiperspirant composition of any one of Aspects 1-38, further comprising a suspending agent.

Aspect 40 provides the antiperspirant composition of Aspect 39, wherein the suspending agent is in a range of from about 0.1 wt % to about 5 wt % of the antiperspirant composition.

Aspect 41 provides the antiperspirant composition of any one of Aspects 39 or 40, wherein the suspending agent is in a range of from about 0.1 wt % to about 2 wt % of the antiperspirant composition.

Aspect 42 provides the antiperspirant composition of any one of Aspects 1-41, further comprising an oil absorbent.

Aspect 43 provides the antiperspirant composition of Aspect 42, wherein the oil absorbent is present in a range of from about 0.001 wt % to about 3 wt % of the antiperspirant composition.

Aspect 44 provides the antiperspirant composition of any one of Aspects 42 or 43, wherein the oil absorbent is present in a range of from about 0.01 wt % to about 0.5 wt % of the antiperspirant composition.

Aspect 45 provides the antiperspirant composition of any one of Aspects 1-44, wherein the combined amount of the isododecane component, alkyl benzoate component, and neopentyl glycol diheptanoate component is substantially equivalent to an amount of cyclopentasiloxane present in a comparative antiperspirant composition differing by comprising cyclopentasiloxane.

Aspect 46 provides the antiperspirant composition of any one of Aspects 1-45, wherein the combined amount of the isododecane component, alkyl benzoate component, and neopentyl glycol diheptanoate component is substantially equivalent to an amount of cyclopentasiloxane present in a comparative antiperspirant composition differing only by comprising cyclopentasiloxane.

Aspect 47 provides the antiperspirant composition of any one of Aspects 45 or 46, wherein an intensity or quantity of spray discharge, amount of residue build-up in an underarm, amount of residue staining of clothing, perceived stickiness, antiperspirant protection, anti-odor protection, softness perception, or a combination thereof of the antiperspirant composition is substantially equal to that of the comparative antiperspirant composition.

Aspect 48 provides a method of making the antiperspirant composition of any one of Aspects 1-47, the method comprising:

combining the isododecane component; alkyl benzoate component; and the neopentyl glycol diheptanoate component.

Aspect 49 provides the antiperspirant composition of any one of Aspects 1-48, wherein the antiperspirant composition comprises an antiperspirant stick, an antiperspirant gel, or an antiperspirant spray.

Aspect 50 provides an assembly comprising:

a spray container; and the antiperspirant composition of any one of Aspects 1-49.

What is claimed is:

1. An antiperspirant composition comprising:

an isododecane in a range of from about 10 wt % to about 30 wt % of the antiperspirant composition;

an alkyl benzoate in a range of from about 15 wt % to about 30 wt % of the antiperspirant composition;

a neopentyl glycol diheptanoate in a range of from about 1 wt % to about 10 wt % of the antiperspirant composition; and PEG-30 dipolyhydroxystearate in a range of about 0.01 wt % to about 5 wt % of the antiperspirant composition, wherein the antiperspirant composition is free of cyclopentasiloxane.

2. The antiperspirant composition of claim 1, wherein the alkyl benzoate is a C12-15 alkyl benzoate.

3. The antiperspirant composition of claim 1, wherein the isododecane, alkyl benzoate, and neopentyl glycol diheptanoate together range from about 30 wt % to about 70 wt % of the antiperspirant composition.

4. The antiperspirant composition of claim 1, wherein the antiperspirant composition is in the form of a stick antiperspirant, a body spray, a clear gel, or an aerosol antiperspirant.

5. The antiperspirant composition of claim 1, further comprising a perfume.

6. The antiperspirant composition of claim 1, further comprising water.

7. The antiperspirant composition of claim 1, further comprising a deodorant active.

8. The antiperspirant composition of claim 1, further comprising an odor entrapping deodorant active.

9. The antiperspirant composition of claim 1, further comprising a buffering agent.

10. The antiperspirant composition of claim 1, further comprising a preservative.

11. The antiperspirant composition of claim 1, further comprising a propellant.

12. The antiperspirant composition of claim 1, further comprising an antiperspirant concentrate.

13. The antiperspirant composition of claim 12, wherein the concentrate comprises an alcohol.

14. The antiperspirant composition of claim 1, further comprising a suspending agent.

15. The antiperspirant composition of claim 1, further comprising an oil absorbent.

16. A method of making the antiperspirant composition of claim 1, the method comprising:

combining the isododecane; alkyl benzoate; neopentyl glycol diheptanoate; and the PEG-30 dipolyhydroxystearate.

17. The antiperspirant composition of claim 1, wherein the antiperspirant composition is in the form of an antiperspirant stick, an antiperspirant gel, or an antiperspirant spray.

18. An assembly comprising:

a spray container; and the antiperspirant composition of claim 1.

\* \* \* \* \*